US005961497A

United States Patent [19]
Larkin

[11] Patent Number: 5,961,497
[45] Date of Patent: Oct. 5, 1999

[54] CONNECTION DEVICE WITH PRE-SLIT SEAL

[75] Inventor: Mark E. Larkin, Lindenhurst, Ill.

[73] Assignee: Abbott Laboratories, Abbott Park, Ill.

[21] Appl. No.: 08/967,193

[22] Filed: Oct. 29, 1997

Related U.S. Application Data

[63] Continuation of application No. 07/805,391, Dec. 10, 1991, abandoned.

[51] Int. Cl.$^6$ ...................................................... A61M 5/00
[52] U.S. Cl. ........................ 604/246; 604/905; 604/201; 604/205
[58] Field of Search ............................ 604/88–91, 181–3, 604/200–2, 205, 236, 237, 240–2, 244, 246, 249, 256, 280, 283, 284, 905

[56] References Cited

U.S. PATENT DOCUMENTS

| | | | |
|---|---|---|---|
| 3,387,609 | 6/1968 | Shields | 604/202 |
| 4,197,848 | 4/1980 | Garrett et al. . | |
| 4,289,129 | 9/1981 | Turner . | |
| 4,378,015 | 3/1983 | Wardlaw | 604/202 |
| 4,578,063 | 3/1986 | Inman et al. . | |
| 4,752,292 | 6/1988 | Lopez et al. . | |
| 4,776,843 | 10/1988 | Martinez et al. . | |
| 4,874,369 | 10/1989 | Kulle et al. . | |
| 4,950,260 | 8/1990 | Bonaldo . | |
| 4,976,925 | 12/1990 | Porcher et al. | 604/202 |
| 5,135,489 | 8/1992 | Jepson et al. | 604/201 |
| 5,199,948 | 4/1993 | McPhee | 604/88 |
| 5,342,316 | 8/1994 | Wallace | 604/201 |

FOREIGN PATENT DOCUMENTS 0019264  11/1980  European Pat. Off. .

*Primary Examiner*—Wynn Wood Coggins
*Assistant Examiner*—Jennifer R. Sadula
*Attorney, Agent, or Firm*—Daniel J. Hulseberg; Brian R. Woodworth

[57] ABSTRACT

A connecting system is provided with a connector adapted to be mounted to the end of a conduit for removably engaging a blunt cannula to establish fluid communication between the conduit and cannula. The connector has a housing which defines a passage for communicating with the conduit and which defines an opening to the passage. The housing also defines a generally frustoconical seating surface which decreases in diameter in the direction toward the opening. A generally fluid-impervious, resilient seal is retained within the housing passage against the seating surface. The seal defines a slit which can accommodate penetration by the blunt cannula and which can reseal upon withdrawal of the blunt cannula.

6 Claims, 2 Drawing Sheets

CONNECTION DEVICE WITH PRE-SLIT SEAL

This application is a continuation of U.S. patent application Ser. No. 07/805,391 filed Dec. 10, 1991, now abandoned.

TECHNICAL FIELD

The present invention relates to connecting systems or coupling systems for connecting fluid conduits together for use in medical procedures. The present invention is particularly well-suited for use in a two-part connecting system in which one part includes a blunt cannula for being sealingly received in the other part.

BACKGROUND OF THE INVENTION AND TECHNICAL PROBLEMS POSED BY THE PRIOR ART

Various medical procedures require the transfer of fluid from one fluid-containment system or fluid-conducting system to another fluid-containment system or fluid-conducting system. Typically, one of the two systems is connected directly to a patient in some manner for a substantial period of time. The other system may be connected to the first system for only a short period of time, or intermittently, to collect an effluent flow of a fluid or fluids from the patient or to supply a fluid or fluids to the patient.

The fluid flow system that is directly connected to the patient may be regarded, for purposes of discussion, as the first system and may include a connection device which can function as a so-called "injection site" for being penetrated by a transferring device such as a hollow needle or cannula of a syringe. A fluid may be dispensed from, or collected by, the syringe needle or cannula through the injection site. The syringe, along with its hollow needle or cannula, and other fluid containers and transferring devices may be regarded in this context as the second fluid flow system.

In other procedures, the first fluid flow system that is connected directly to the patient may be engaged with an appropriate cannula or other conduit that is part of a second fluid flow system which also includes flexible tubing connected to either a receiving container (e.g., collection bag) or a supply reservoir (e.g., container of a liquid agent to be introduced into the patient).

It is usually desirable, where possible, to avoid the use of a needle or sharp cannula. A person using, or exposed to, a needle may accidentally puncture his or her skin, or may accidentally puncture the skin of another person. Because such a needle may have been used in patient treatment procedures and/or otherwise brought into contact with patient fluids or other contaminants, there is a risk of becoming infected as a result of such an accidental puncture. Likewise an accidental puncture may result in an adverse reaction to a drug used in IV therapy. Accordingly, there is great interest in developing and using systems which can eliminate, where possible, the use of a hollow needle or sharp cannula to establish fluid flow connections.

Connection devices for use with a blunt cannula, which do not puncture the skin, have been disclosed in U.S. Pat. No. 4,197,848 and in published Patent Cooperation Treaty international patent application No. PCT/US89/00273 (International Publication No. WO 89/06553). U.S. Pat. No. 4,197,848 discloses an irrigation site which has a resilient membrane with a slit for accommodating penetration by a blunt end syringe. The resilient membrane extends generally transversely across a passage in a housing in which the membrane is mounted, and the periphery of the membrane includes a generally cylindrical skirt for being retained in an annular channel of the housing.

International patent application No. PCT/US89/00273 discloses a variety of embodiments of a system which includes an injection site for a blunt cannula. The site employs a housing having a distal end defining an opening for accommodating insertion of the blunt cannula. In most of the disclosed embodiments, an annular, tapered, interior surface is defined by the housing inwardly of the opening, and the diameter of the tapered surface decreases with increasing distance away from the opening at the distal end of the housing. A resilient septum having a slit is provided to engage the tapered interior surface of the housing. The end of the housing is swaged against the periphery of the septum to apply axial forces to the septum while the internal, tapered surface of the housing applies radially directed forces to the septum for forcing the septum slit into a resealed condition. FIG. 27 of the application discloses an alternate, non-tapered embodiment which is described as providing "compression to create a seal against pressure and a void region to accommodate deformed portions of the sealing member material only when the material is deformed or displaced by a blunt cannula piercing member."

Although the above-discussed connection device and injection site designs may function satisfactorily in certain applications—within certain pressure ranges and with certain sizes and configurations of cannula—it would be desirable to provide an improved connection device offering advantages and features that have been heretofore unavailable.

In particular, it would be desirable to provide an improved connection device which could be manufactured without requiring the imposition of extremely strict and critical manufacturing tolerances. It would be beneficial if such an improved device could be manufactured within a range of tolerances without deleteriously affecting its performance or without degrading the sealing and resealing integrity or capability of the device.

Further, in view of the danger of contamination and infection, it would be desirable to provide a connection device which would facilitate its use as a disposable item. To this end, the improved device should be relatively inexpensive. Accordingly, the device should incorporate an improved component design that accommodates relatively simple manufacturing processes and assembly processes so as to keep the total cost as low as possible.

An improved connection device should also function to effectively seal around a blunt cannula, as well as reseal after the cannula is removed, so as to prevent unwanted leakage of fluids and so as to prevent ingress of airborne or liquid-carried contaminants.

The improved device should also preferably accommodate use with a variety of fluids throughout a range of fluid pressures.

Advantageously, the improved device should have a suitably long shelf life and active use life. Further, it should function effectively after repeated penetrations and removals of a blunt cannula.

Finally, it would be desirable for such an improved connection device to facilitate handling and use by medical personnel. In particular, the device should accommodate initial insertion of a blunt cannula, should provide engaging forces and/or latches sufficient to prevent inadvertent withdrawal of the cannula, and should nevertheless permit the cannula to be withdrawn by appropriate manipulation.

The present invention provides an improved connection device which can accommodate designs having the above-discussed benefits and features.

SUMMARY OF THE INVENTION

The present invention provides a novel connector or connection device, as well as a connecting system, for establishing fluid communication between two fluid flow conduits. Although the invention may function well where one of the conduits is a hollow sharp needle, the invention is intended to be primarily and advantageously used with a blunt, rigid conduit, such as a blunt cannula or the like. The invention accommodates the use of a blunt cannula so as to avoid the risk of accidental skin puncture that exists with a hollow needle or a sharp cannula. The invention may be employed to connect two flexible tubing systems or may be employed to at least temporarily connect, or establish communication between, a syringe and another conduit system.

The connection device of the present invention incorporates a novel design which permits the device to be relatively inexpensively manufactured. The design does not require excessively strict tolerances in order to provide an effective sealing function or contaminant barrier function. The design accommodates a variety of fluids, pressures, and component sizes.

The components employ a unique design which facilitates their use, including facilitating the insertion of a blunt cannula, facilitating the engagement of the cannula so as to help prevent inadvertent withdrawal, and facilitating removal of the cannula in a relatively easy manner that permits the system to reseal for preventing fluid ingress or egress or internal contamination.

According to one aspect of the invention, a connection device or connector is provided that is suitable for mounting to the end of a first conduit. The connector can removably engage another conduit, including a blunt cannula, so as to establish fluid communication between the two conduits.

The connector includes a housing defining a passage for communicating with the first conduit. The housing has a distal end defining an opening to the passage, and the housing defines a generally frustoconical seating surface which decreases in diameter in the direction toward the opening.

A generally fluid-impervious, resilient membrane or seal is retained within the housing passage against the seating surface. The seal defines an aperture or slit through the seal which can accommodate penetration by the other conduit, including a blunt cannula, and which can reseal upon withdrawal of the blunt cannula or other similar type of conduit.

In a preferred form of the invention, the housing is a two-piece structure which includes a first housing section and a second housing section which are joined together to clamp the seal in place.

According to a further aspect of the invention, the connector can be incorporated in a connecting system suitable for coupling a first conduit to a second conduit through a blunt cannula that has a proximal end and a distal end. The housing defines a passage for communicating with the first conduit and has a proximal end for being mounted to the first conduit. The housing has a distal end defining an opening to the passage. The housing defines a generally frustoconical seating surface which decreases in diameter in the direction toward the opening.

A seal of the type described above is retained within the housing passage against the seating surface.

The system further includes a frame in which the blunt cannula is carried to accommodate mounting of the proximal end of the blunt cannula to the second conduit to establish fluid communication between the second conduit and blunt cannula. The frame preferably includes a latch means for engaging the connector housing when the blunt cannula is inserted through the seal.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENTS

While this invention is susceptible of embodiment in many different forms, this specification and the accompanying drawings disclose only one specific form as an example of the invention. The invention is not intended to be limited to the embodiment so described, however. The scope of the invention is pointed out in the appended claims.

For ease of description, the connector and connecting system of this invention are described in an arbitrarily selected operating position, and terms such as upper, lower, horizontal, etc., are used with reference to this position. It will be understood, however, that the components of this invention may be manufactured, stored, transported, used, and sold in an orientation other than that described.

Some of the figures illustrating embodiments of the components show some structural details that will be recognized by one skilled in the art. However, the detailed descriptions of such details are not necessary to an understanding of the invention, and accordingly, are not herein presented.

The connector and connecting system of this invention are typically used with certain conventional components the details of which, although not fully illustrated or described, will be apparent to those having skill in the art and an understanding of the necessary functions of such components.

The connector and connecting system of the present invention provide design advantages and operational advantages. The connector and connecting system incorporate a resilient membrane or seal installed in a housing in a unique manner that does not require the type of radial compression fit taught by some of the prior art. Rather, a special tapered configuration permits the sealing function of the membrane or seal to be enhanced by internal pressure, and the novel tapered configuration also facilitates component fabrication and assembly.

Figure 1:
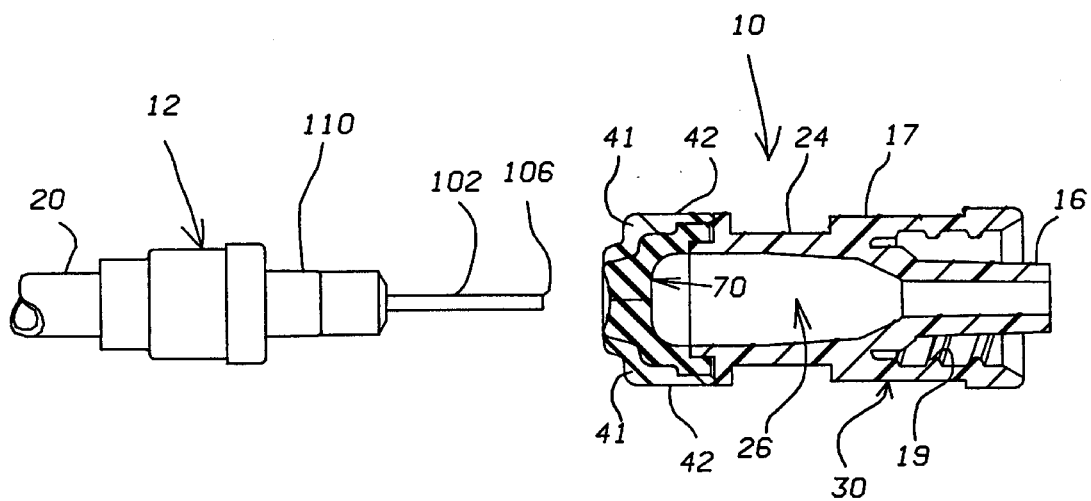
FIG. 1 is a cross-sectional view of an embodiment of the components of the connecting system of the present invention prior to the components being engaged.
Figure 2:
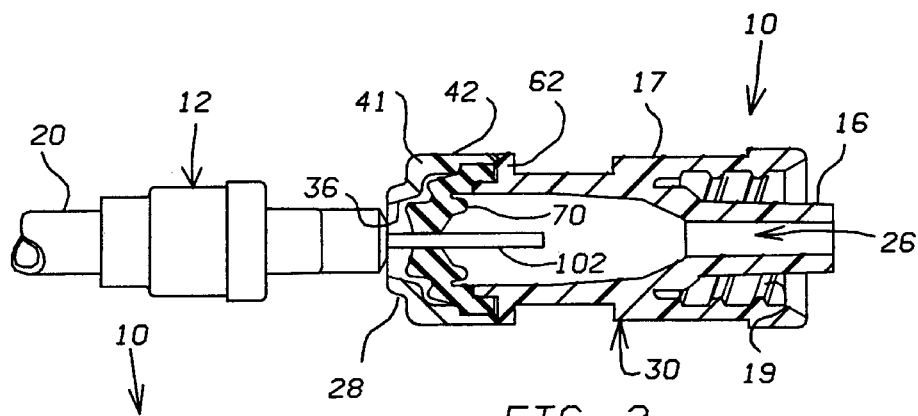
FIG. 2 is a view similar to FIG. 1, but FIG. 2 shows the components engaged.
Figure 3:
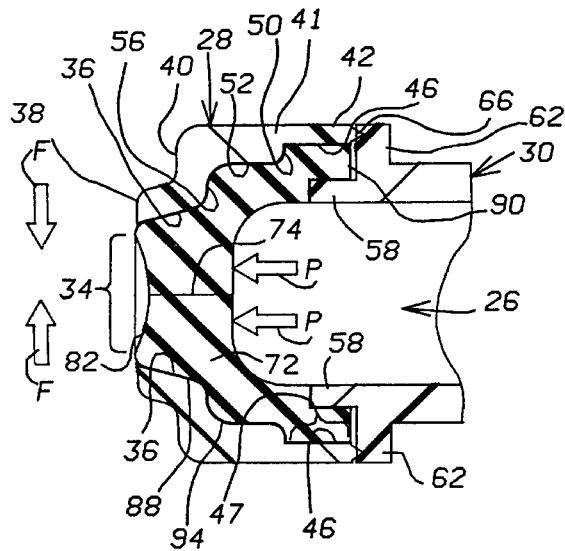
FIG. 3 is a greatly enlarged, fragmentary, cross-sectional view of the connector component that is shown on the right-hand side of FIG. 1.

A first embodiment of a connecting system in accordance with the present invention is illustrated in FIGS. 1–3. The system includes the connector 10 which is adapted to be engaged with a cannula assembly 12. The cannula assembly 12 is adapted to be engaged with the connector 10 in the coupled configuration as illustrated in FIG. 2 so as to establish fluid communication between the assembly 12 and the connector 10.

The connector 10 has a proximal end defined, in part, by a rigid tube 16 which is adapted to be mounted, connected, attached, or otherwise joined to an end of a first conduit (not illustrated) so as to establish fluid communication between such a first conduit and the interior of the connector 10. If desired, and as illustrated in FIGS. 1 and 2, the connector 10 may include a rearwardly extending skirt 17 defining a thread form 19 for threadingly engaging a cooperating member or fitting on a tube, container, or other equivalent, fluid-containing conduit.

The assembly 12 has a proximal end which is defined by a rigid tube 20 which is adapted to be mounted, attached, connected, or otherwise joined to a second conduit (not illustrated).

Typically, the first conduit to be connected to the connector 10 and the second conduit to be connected to the assembly 12 would be a type of flexible, thermoplastic tubing of the kind commonly used in medical procedures and which serve to accommodate the passage of a fluid or fluids into or out of a patient. It is to be realized, however, that the connector 10 and assembly 12 of the illustrated system may each be connected to a rigid conduit or to other rigid, fluid-containment systems which would be equivalent to such a rigid conduit. In such a situation, means would have to be provided to permit or accommodate movement of at least one of the rigid conduit systems with the attached connector 10 or attached assembly 12 so as to accommodate relative movement between the connector 10 and assembly 12 to establish the coupled orientation illustrated in FIG. 2.

The connector 10 includes a housing 24 which defines a central passage 26 for communicating, through the tube 16, with the first conduit (not illustrated) that may be attached to the tube 16. The housing 24, in the preferred embodiment illustrated, includes a first housing section 28 and a second housing section 30 which are suitably joined together (as with adhesive, by spin welding, etc.).

As best illustrated in FIG. 3, the first housing 28 has a distal end defining an opening 34 for communicating with the passage 26. The first housing section 28 also defines a frustoconical seating surface 36 which surrounds the opening 34 and which increases in diameter with increasing distance from the opening 34. Alternatively, the frustoconical seating surface 36 may be characterized as decreasing in diameter in the direction toward the opening 34. In a presently contemplated preferred commercial embodiment, the sealing surface 36 defines an angle of about 20 degrees relative to the longitudinal axis about which the surface 36 is oriented.

The first housing section 28 has a generally annular configuration with an outwardly projecting first portion 38, a radially extending shoulder 40, and a skirt 41 having a generally cylindrical, exterior surface 42.

On the interior of the first housing section 28 there is a generally cylindrical, recessed, retaining surface 46 which defines a peripheral retaining cavity 47. The cylindrical retaining surface 46 and the adjacent retaining cavity 47 are located axially inwardly beyond the seating surface 36. Between the cylindrical retaining surface 46 and the seating surface 36, the first housing section 28 defines an interior annular shoulder 50 which extends radially inwardly from the retaining surface 46. The inner edge of the shoulder 50 is defined by a generally cylindrical surface 52 which merges with the seating surface 36 via an intermediate shoulder 56.

With continued reference to FIG. 3, the second housing section 30 has an interior, annular, engaging wall 58 which is spaced radially inwardly of the first housing section retaining surface 46. The wall 58 extends axially adjacent at least a part of the retaining cavity 47 so that part of the cavity 47 is defined between the retaining surface 46 and the wall 58.

As illustrated in FIG. 3, the second housing section 30 also defines a radially extending, exterior flange 62. The distal end of the first housing section skirt 41 defines a sealing bead or ridge 66 for engaging a surface of the flange 62. The flange 62 may be provided with a groove for accommodating the sealing ridge 66. Alternatively, the flange 62 may be slightly deformed by the sealing ridge 66 in a shear welding or sonic welding process so as to insure a tight engagement between the first housing section 28 and the second housing section 30.

The first housing section 28 and the second housing section 30 may be fabricated from the same materials or different materials that are suitable for the intended operating conditions. This contemplates, of course, the nature of the fluids to be passed through the connector 10, the operating temperatures and pressures, the nature of the exterior ambient atmosphere, the type of fluids that may contact the exterior of the connector 10 and other parts. Suitable materials include polyester, acrylic, polycarbonate, and polystyrene. In a presently contemplated, proposed, commercial design, the preferred material for the first housing section 28 is polystyrene, and the preferred material for the second housing section 30 is polystyrene.

A novel barrier, membrane, or seal 70 is mounted within the housing section 28 and is retained therein by the second housing section 30 as illustrated in FIG. 3. The seal 70 is generally fluid-impervious and functions as a barrier against liquid-carried contaminants and airborne contaminants.

The membrane seal 70 is fabricated from a resilient material which may be a synthetic elastomer or other suitable material such as silicone rubber, or natural rubber. Preferably, the seal material is compatible with the fluids with which the system is intended to be operated, and the seal material is preferably of the type that can be sterilized by means of radiation, steam, or ethylene oxide. In a preferred form, the seal 70 is natural rubber.

The seal 70 includes a central body portion 72 defining an aperture or slit 74 which extends completely through the body portion 72. As used in this specification and in the appended claims, the term "slit" means a penetration, path, or other type of aperture that is normally closed (owing to the inherent resiliency or biasing action of the seal material) and that can be forced to an open condition by insertion of an instrument such as a blunt cannula. Withdrawal of such an instrument allows the residual bias or inherent resiliency of the material to close the penetration site defined by the slit 74. This prevents ingress of unwanted contaminants and prevents egress of materials contained in the interior of the connector 10.

The seal 70 may have a generally concave, exterior surface 82 at the opening 34 in the first housing section 28. This can serve as a means for guiding an instrument, such as a blunt cannula, toward the slit 74.

The seal central body portion 72 defines a peripheral, frustoconical surface 88 which generally corresponds to, and which is adapted to be disposed in mating engagement with, the first housing section seating surface 36.

The seal 70, because it defines the slit 74 which can be opened by an appropriate penetrating instrument, and because the slit 74 closes upon withdrawal of the instrument, is sometimes characterized in the art as a "reseal". However, in this specification and in the appended claims, the term "seal" will be used with the understanding that the seal 70 functions to (1) seal closed the housing opening 34 in the absence of a penetrating member, (2) seal around the exterior of the penetrating member that is inserted through the seal slit 74, and (3) re-close or re-seal the opening 34 upon withdrawal of the penetrating instrument from the slit 74.

The seal 70 also includes a mounting flange 90 which extends from the central body portion 72 and which is adapted to be received in the first housing section retaining cavity 47 adjacent the retaining surface 46. The flange 90 is clamped in that location by the annular engaging wall 58 of the second housing section 30.

Further, as illustrated in FIG. 3, the seal 70 preferably includes an intermediate shoulder portion 94 joining the mounting flange 90 to the central body portion 72. The shoulder portion 94 generally conforms to the first housing section surfaces 52 and 56 that extend between the retaining surface 46 and the frustoconical seating surface 36.

With reference to FIG. 3, it will be appreciated that the novel design functions to effectively seal the housing opening 34. The tapered or frustoconical seating surface 36 of the housing functions to increase the sealing force on the slit 74 as indicated by the arrows designated by the reference letter F in FIG. 3. Further, when the interior of the connector 10 is subjected to fluid pressure, that fluid pressure acts upon the inner surface of the seal 70 around the slit 74 as illustrated by the arrows designated by the reference letter P in FIG. 3. This can improve the sealing action to prevent egress of fluids through the slit.

An instrument which may be employed for insertion into the seal 70 for penetrating the slit 74 is a blunt cannula, and such a blunt cannula is designated by the reference numeral 102 in FIGS. 1 and 2 wherein the blunt cannula 102 is incorporated as a unitary part of the assembly 12. As used in the specification and in the appended claims the term "cannula" is intended to include any conduit means for performing the same insertion and fluid transfer functions that are preformed by a cannula.

As illustrated in FIG. 1, the blunt cannula 102 has a distal end 106 and has a proximal end which is in fluid communication with the above-described rigid tube 20 extending from the proximal end of the assembly 12 and to which a flexible tube (or other conduit system) may be connected. The cannula 102 is carried by a frame or housing 110. The frame or housing 110 is fixed to the cannula 102 to prevent axial or rotational movement of the cannula.

When the assembly 12 and connector 10 are coupled together as is illustrated in FIG. 2, the distal end 106 of the cannula 102 penetrates the seal 70. The seal 70 is deflected and deformed inwardly from the housing opening 34 within the passage 26. As can be seen in FIG. 2, the seal 70 is forced away from some interior surfaces of the first housing section 28, such as the frustoconical seating surface 36. The space within the first housing section 28, including a portion of the passage 26, accommodates the distortion of the seal 70. The deformed and distorted seal 70 tightly grips the surface of the cannula 102 and provides a sealing engagement around the cannula 102 to prevent leakage.

When the assembly 12 is disconnected from the connector 10 and the cannula 102 is withdrawn, the seal 70, owing to its inherent resiliency (residual bias), returns to the original, substantially undeformed condition illustrated in FIGS. 1 and 3. The tapering configuration of the frustoconical seating surface 36, in cooperation with the mating frustoconical surface 88 of the seal 70, effects a closure of the slit 74 and prevents leakage through the seal 70 as well as ingress of contaminants.

The assembly 12 may be fabricated from the same materials as described above for use in fabricating the connector housing sections 28 and 30.

Figure 4:
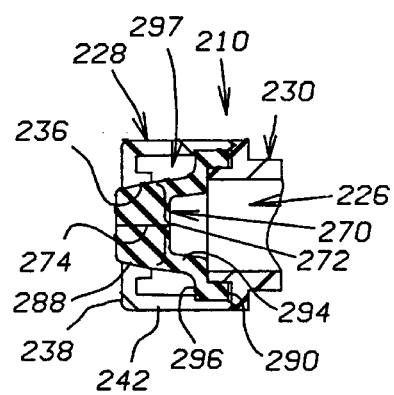
FIG. 4 is a view similar to FIG. 3, but FIG. 4 shows an alternate embodiment.

An alternate embodiment of the connector 10 is illustrated in FIG. 4 wherein the connector is designated by the reference numeral 210. The connector 210 includes a first housing section 228 and a second housing section 230. The second housing section 230 may be substantially identical to that described above with reference to the first housing section 30 illustrated in FIGS. 1, 2, and 3.

The first housing section 228 has a generally cylindrical wall 242 and a generally disk-like, end wall 238 at the distal end of the housing section 228. The end wall 238 has an opening defined by a frustoconical seating surface 236. The diameter of the surface 236 increases in the direction away from the opening at the distal end of the housing section 228.

A seal 270 is provided within the first housing section 228 and has a central body portion 272 which defines a frustoconical surface 288 that generally conforms to, and matingly engages, the first housing section seating surface 236. Further, a slit 274 is defined completely through the seal body central portion 272.

The seal 270 includes an inwardly extending skirt 294, a flange 296 extending radially from the end of the skirt 294, and a mounting flange 290 extending from the radial flange 296. The mounting flange 290 is engaged between portions of the first housing section 228 and the second housing section 230 in substantially the same manner as described above with respect to the first embodiment of the seal 70 illustrated in FIGS. 1–3. The housing sections 228 and 230 are suitably secured together (by adhesive, welding, or the like), and define an internal passage 226 which communicates at one end with the seal slit 274 and which communicates at the other end with tubing or with other conduit (not illustrated) attached to the end of the second housing section 230.

Owing to the generally annular, cylindrical configuration of the first housing section wall 242, there is an additional space or volume 297 within the first housing section 228 adjacent the seal 270. This accommodates additional deformation or distortion of the seal 270 when a cannula is inserted into the seal slit 274.

Figure 5:
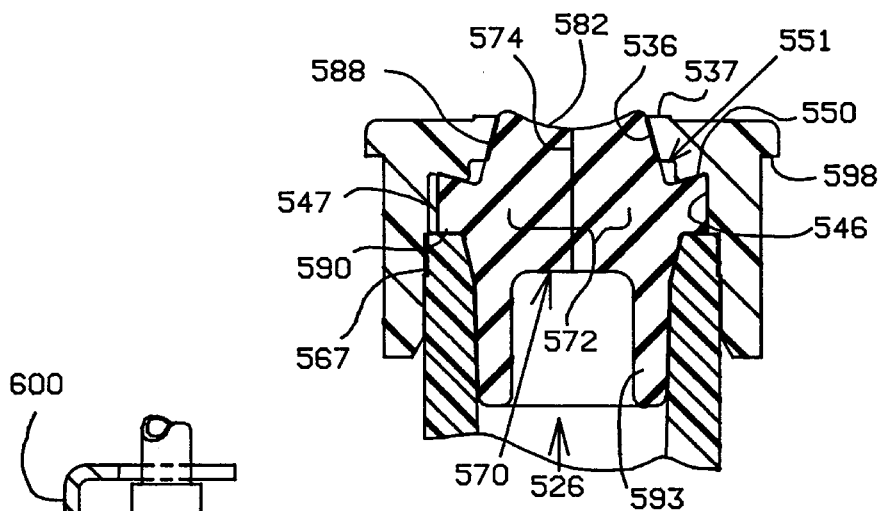
FIG. 5 is a view similar to FIG. 3, but FIG. 5 shows yet another embodiment.
Figure 6:
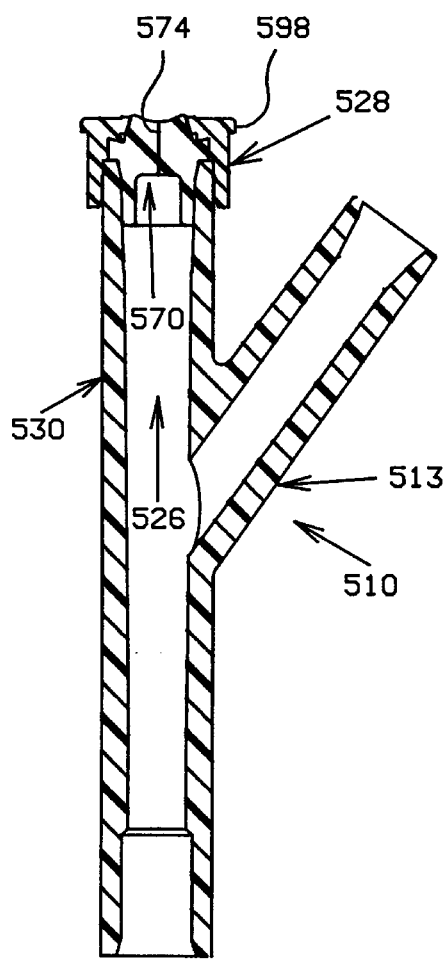
FIG. 6 is a cross-sectional view, on a reduced scale, of the connector of FIG. 5 installed in a Y-site.

FIGS. 5 and 6 illustrate another embodiment of the connector of the present invention. FIG. 6 illustrates how the connector may be incorporated in a Y-site connector which is designated by the reference numeral 510. The Y-site connector 510 includes a conventional straight run housing section 530 and a 45 degree angle branch section 513. The branch section 513 may include certain conventional internal components, including a membrane or seal injection site or connection device.

As best illustrated in FIG. 5, a resilient seal 570 is mounted at the end of the Y-site straight run housing section 530. The Y-site straight run housing section 530 may be characterized as being analogous to the second housing section 30 described above with reference to the first embodiment illustrated in FIGS. 1–3. The Y-site straight run section 530 defines an internal passage 526. The seal 570 is retained on the section 530 at the end of the passage 526 by means of a housing section 528 which is analogous to the first housing section 28 described above with reference to the first embodiment illustrated in FIGS. 1–3. The first housing section 528 may be shear welded or sonic welded to the housing section 530 by means of a shear weld as indicated by the interference at 567.

The housing section 528 has an opening that communicates with the passage 526, and a generally frustoconical seating surface 536 extends inwardly from the opening. The seating surface 536 increases in diameter in the direction away from the opening.

The seal 570 has a central body portion 572 which defines a slit 574 extending completely through the central body portion 572. The central body portion 572 also has a concave, exterior surface 582. The peripheral, circular margin of the concave surface 582 projects slightly beyond the end of the housing section 528. The housing section 528 preferably defines a raised, annular ring 537 around the seal's concave surface 582. The ring 537 functions as a target ring, and can be hot stamped on the housing section 528 if the housing section 528 is molded from a thermoplastic material.

The housing section 528 defines an interior, cylindrical retaining surface 546 (FIG. 5). The first housing section 528 also includes a frustoconical shoulder 550 which extends generally radially inwardly from, as well as away from, the distal end of the housing section 528. A retaining cavity 547 is defined by the shoulder 550, the retaining surface 546, and the end of the housing section 530.

The seal 572 also includes a mounting flange 590 for being received in the retaining cavity 547. As illustrated in FIG. 5, the surfaces of the seal flange 590 substantially conform to the surfaces of retaining cavity 547 defined by the end of the housing section 530, the retaining surface 546, and the frustoconical shoulder 550. In addition, the inwardly angled configuration of the frustoconical surface 550 provides a dove tail engagement of the seal flange 590 to aid in retaining the flange 590 in place. The seal 572 also includes an inwardly projecting skirt 593. The skirt 593 extends along the passage defined by the housing section 530.

The seal central body portion 572 defines a peripheral, frustoconical surface 588 which substantially conforms to, and matingly engages, the frustoconical seating surface 536. The engagement of the seal 570 with the first housing section 528 along the mating frustoconical surfaces serves to seal the slit 574 and increases the slit closure force as internal pressure increases within the passage 526.

The edge of the frustoconical shoulder 550 is located a small distance radially outwardly beyond the seal frustoconical surface 588. This defines a space or void 551 adjacent the seal 572. The void 551 accommodates displacement of the seal 570 when a cannula is inserted through the slit 574. The void 551 also accommodates travel of the tapered region of the seal 570 so as to improve the resealing action.

If desired, the first housing section 528 can be provided with an exterior flange 598 as illustrated in FIGS. 5 and 6 to accommodate automated handling of the component.

Figure 7:
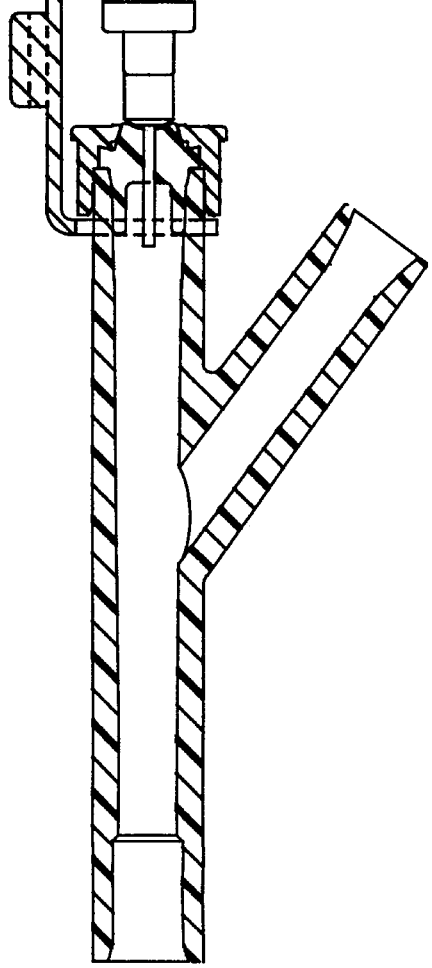
FIG. 7 is a partial cross-sectional view of an embodiment of the connecting system of the present invention including a latching mechanism.

Since it is desirable to prevent the inadvertent disconnection of the two connectors, a latching mechanism can easily be added to either or both connectors to insure that the connectors remain engaged. FIG. 7 discloses for example a bracket member 600 that snaps over radially protruding flanges on both connectors to reduce their relative axial movement once connected. Alternatively, either connector could include resilient latches integral with the connector housing or frame. For example, resilient fingers may extend generally parallel to the cannula and have a lip at the distal end which extends radially inward to engage the housing of the other connector.

The connector and connecting system of the present invention provide an improved design which accommodates relatively inexpensive fabrication and assembly techniques. The components can be relatively easily manufactured within tolerances that are not extremely critical, and the assembled components function effectively to provide the intended sealing functions, even after repeated use.

The novel design does not rely on a conventional compression fit of a resilient seal member to establish sealing. Further, the sealing is improved by internal pressure acting upon the seal engaged with the novel tapered configuration of the retention housing.

It will be readily apparent from the foregoing detailed description of the invention and from the illustrations thereof that numerous variations and modifications may be effected without departing from the true spirit and scope of the novel concepts or principles of this invention.

What is claimed is:

1. A connector suitable for mounting to the end of a first conduit and for removably engaging another conduit to establish fluid communication between the first conduit and the other conduit, said connector comprising:

a housing defining a passage having first and second open ends and having a longitudinal axis, said first open end constructed for mounting to the end of a conduit, said housing defining a generally frustoconical seating surface located within said housing passage at said second open end and oriented around said longitudinal axis of said passage, said seating surface increasing in diameter in the direction away from said second open end, said frustoconical seating surface and said longitudinal axis of said passage defining an angle open in the direction away from said second open end, said housing further defining a peripheral retaining cavity located in the interior of said housing and between said seating surface and said first open end, said housing peripheral retaining cavity having a diameter greater than the largest diameter of said seating surface; and a generally fluid-impervious, resilient seal retained within said housing passage against said seating surface, said seal defining a frustoconical surface generally conforming to, and engaged with, said seating surface, said seal defining a slit through said seal, said slit having first and second ends, said slit first end in fluid communication with said housing passage and said slit second end positioned within said passage second open end.

2. The connector in accordance with claim 1, wherein the angle defined between said frustoconical seating surface and said longitudinal axis of said passage is an acute angle.

3. The connector in accordance with claim 2, wherein the acute angle defined between said frustoconical seating surface and said longitudinal axis of said passage is about 20 degrees.

4. A connector suitable for mounting to the end of a conduit and removably engaging a blunt cannula to establish fluid communication between the conduit and the blunt cannula, said connector comprising:

a first housing section defining first and second open ends and having a longitudinal axis, said first housing section defining a generally frustoconical seating surface that is located on the interior of said first housing section, surrounds said second open end, is oriented around said longitudinal axis of said first housing section and increases in diameter with increasing distance from said second open end, said first housing section further defining a peripheral retaining cavity located on the interior of said first housing section and between said seating surface and said first open end, said first housing section peripheral retaining cavity having a diameter greater than the largest diameter of said seating surface;

a generally fluid-impervious, resilient seal, said seal having a central body portion defining a frustoconical surface generally corresponding to, and in engagement with, said first housing section seating surface, said central body portion further defining a slit through said seal, said slit having first and second ends, said slit first end positioned within said first open end of said first housing section and said slit second end positioned within said second open end of said first housing section, said seal further including a mounting flange extending from said central body portion for being received in said first housing section peripheral retaining cavity; and a second housing section joined to said first housing section, said second housing section defining an interior passage, said passage in fluid communication with said slit first end, said second housing section defining a generally annular engaging wall for holding said seal mounting flange in said first housing section peripheral retaining cavity, said second housing section annular engaging wall spaced radially inwardly of said first housing section peripheral retaining cavity and axially located adjacent at least part of said first housing section peripheral retaining cavity.

5. The connector in accordance with claim 4 in which said frustoconical seating surface and said longitudinal axis of said first housing section define an acute angle open in the direction away from said first housing section second open end.

6. The connector in accordance with claim 5, wherein the acute angle defined between said frustoconical seating surface and said longitudinal axis of said passage is about 20 degrees.

\* \* \* \* \*